United States Patent [19]

Hagen et al.

[11] Patent Number: 5,171,917
[45] Date of Patent: Dec. 15, 1992

[54] SELECTIVE PRODUCTION OF A P-ALKYLETHYLBENZENE OR 4,4'-ALKYLETHYLBIPHENYL

[75] Inventors: Gary P. Hagen, West Chicago, Ill.; Deborah T. Hung, Cambridge, Mass.

[73] Assignee: Amoco Corporation, Chicago, Ill.

[21] Appl. No.: 544,274

[22] Filed: Jun. 26, 1990

[51] Int. Cl.$^5$ .............................................. C07C 5/22
[52] U.S. Cl. ................................... 585/472; 585/471; 585/474
[58] Field of Search ....................... 585/471, 472, 474

[56] References Cited

U.S. PATENT DOCUMENTS

| | | | |
|---|---|---|---|
| 2,388,758 | 11/1945 | Mills, Jr. | 585/474 |
| 4,454,364 | 6/1984 | Farcasiu et al. | 585/472 |
| 4,873,386 | 10/1989 | Hagen et al. | 585/472 |
| 4,950,824 | 8/1990 | Shiroto et al. | 585/474 |

FOREIGN PATENT DOCUMENTS 0116353 10/1978 Japan.

Primary Examiner—Patrick P. Garvin
Assistant Examiner—E. D. Irzinski
Attorney, Agent, or Firm—Thomas E. Nemo; Wallace L. Oliver; Frank J. Sroka

[57] ABSTRACT

A method for the highly selective production of a p-alkylethylbenzene or 4,4'-alkylethylbiphenyl involving the use of a Lewis acid or Bronsted acid alkylation catalyst and a highly regiospecific ethylating agent.

16 Claims, No Drawings

SELECTIVE PRODUCTION OF A P-ALKYLETHYLBENZENE OR 4,4'-ALKYLETHYLBIPHENYL

BACKGROUND OF THE INVENTION

1. Field of the Invention

This invention relates generally to the production of a p-alkylethylbenzene or a 4,4'-alkylethylbiphenyl and more particularly concerns the highly selective production of p-ethyltoluene or p-diethylbenzene by the transethylation of benzene, toluene or ethylbenzene or the production of 4,4'-diethyl- or methylethylbiphenyl by the transethylation of biphenyl, 4-methylbiphenyl or 4-ethylbiphenyl.

2. Description of the Prior Art

Dialkylbiphenyls are useful as high temperature heat transfer media. Dialkylbiphenyls, as well as dialkylbenzenes, are also desirable feedstocks for oxidation to the corresponding biphenyl or benzene dicarboxylic acids, which in turn are monomers that are known to be useful for the preparation of a variety of polymers. A known conventional process for producing a benzene dicarboxylic acid or a biphenyl dicarboxylic acid comprises the oxidation of a dialkylbenzene or a dialkylbiphenyl, respectively, with oxygen in the liquid phase in an acetic acid solvent at an elevated temperature and pressure and in the presence of a catalyst comprising cobalt, manganese and bromine components. In such cases, it is highly desirable that the alkyl groups on the benzene or biphenyl ring are methyl or ethyl.

Thus, there is a need for p-dialkylbenzenes and 4,4'-dialkylbiphenyls and for highly selective processes for making specific p-dialkylbenzenes or 4,4'-dialkylbiphenyls. Because of the great difficulty and expense of separating a p-dialkylbenzene or a 4,4'-dialkylbiphenyl from its other dialkylbenzene isomers or other dialkylbiphenyl isomers, respectively, methods for producing a specific p-dialkylbenzene or 4,4'-dialkylbiphenyl or mixtures of two or three specific p-dialkylbenzenes or 4,4'-dialkylbiphenyls in high purity and quality are especially desirable. One such method is disclosed in Japanese Kokai Patent Application Publication No. 62-252733 (Nov. 4, 1987) and is a process for the transethylation of biphenyl with an ethylbenzene or ethyltoluene to form monoethylbiphenyl and diethylbiphenyl in the presence of a Friedel-Crafts catalyst, such as aluminum chloride, at 70°-150° C. This published Japanese patent application discloses that reaction temperatures of less than 70° C. delay the reaction rate. The ring positions of the ethyl substituents in the ethylated biphenyl products are not disclosed. Suitable ethylbenzenes and ethyltoluenes include ethylbenzene, diethylbenzene, triethylbenzene, tetraethylbenzene, other ethyl-substituted benzenes, ethyltoluene, diethyltoluene and other ethyl-substituted toluenes. Polyethylbenzenes containing relatively small amounts of monoethylbenzene, triethylbenzene and tetraethylbenzene can also be used advantageously.

Japanese Patent Application 35/391/48, published on Oct. 18, 1989, discloses a method for the preparation of ethyldiphenylethane or diethyldiphenylethane by the transethylation of diphenylethane with polyethylbenzene(s) in the presence of a Friedel-Crafts catalyst at 0°-150° C. Preferred catalysts are aluminum chloride, aluminum bromide and boron trifluoride. Transethylation of 1,1-diphenylethane by this method produces either 1-phenyl-1-ethylphenylethane, 1-phenyl-1-diethylphenylethane or 1,1-bis(ethylphenyl)ethane. The ring positions of the ethyl substituents in the ethylated products are not disclosed.

With regard to a different aromatic ring system, Olah et al., "Alkylation of Naphthalene with Alkyl Halides," Journal of American Chemical Society, 98:7, pages 1839–1842 (Mar. 31, 1976), disclose that theretofore there was no clear understanding of directive effects and selectivities for the Friedel-Crafts alkylation of naphthalene. Olah et al. disclose poor selectivities and/or low conversions for the direct methylation of naphthalene or 2-methylnaphthalene using simple methylating agents such as methyl halides or methanol to provide beta-substituted products such as 2,6-dimethylnaphthalenes.

Since then, Japanese Kokai Patent Application Publication No. 61-83137 (Apr. 26, 1986) discloses a synthesis involving the transalkylation of naphthalene or 2-methylnaphthalene in the presence of an aluminum chloride catalyst at 0°-35° C. in the liquid phase to produce a 2,6-dialkylnaphthalene. Suitable alkylating agents are disclosed as including durene, diethylbenzene, triethylbenzene, triisopropylbenzene and isopropylxylene and dibutylbenzene. The reported results indicate a relatively low degree of selectivity for the formation of specific dialkylnaphthalenes. Furthermore, it is specifically stated that the disclosed alkylation method must be performed at 0°-35° C., preferably room temperature, and that the higher the reaction temperature, the lower the selectivity for the formation of beta-alkyl-substituted naphthalene and especially 2,6-dialkylnaphthalene. In addition, although this published patent application specifically mentions durene (1,2,4,5-tetramethylbenzene) as an example of an alkylation agent, it contains actual examples that illustrate only the use as alkylating agents in the method disclosed therein of polyalkylbenzenes where the alkyl groups are larger than methyl groups and indicates as follows that polyalkylbenzenes with alkyl groups other than methyl groups afford benefits in the method disclosed therein: "Polyalkylbenzenes with ethyl, propyl, or butyl groups with high-carbon alkyl groups have high reaction rates ..." Moreover, this published Japanese patent application states that, when the naphthalene is solid at the reaction temperature, a solvent such as a paraffin or cycloparaffin should be employed. This published patent application discusses the use of halogenated alkyls in the alkylation of naphthalenes as a prior art method which did not produce a beta-alkyl naphthalene with the desired selectivity.

Shimada et al., "Ethylation and Transethylation of Naphthalene," Bulletin of the Chemical Society of Japan, Vol. 48 (II), pages 3306–3308 (November 1975), disclose the transethylation of naphthalene by ethylbenzene or ethylxylenes to form monoethylnaphthalenes in the presence of an aluminum chloride catalyst at 20°-30° C. The rates of transethylation with ethylxylene isomers were reported to decrease in the order of 1,2-dimethyl-4-ethylbenzene ≧ 1,3-dimethyl-4-ethylbenzene > 1,4-dimethyl-2-ethylbenzene ≧ 1,3-dimethyl-5-ethylbenzene.

Thus, until recently, no existing method was known for the highly selective production of 2,6-diethylnaphthalene or a mixture of 2,6- and 2,7-diethylnaphthalenes by a transethylation process. Then Hagen et al., U.S. Pat. No. 4,873,386, which issued on Oct. 10, 1989, disclosed a method for producing 2,6-diethylnaphthalene, which comprises: reacting in the liquid phase at least one of naphthalene or 2-ethylnaphthalene as the feed with at least one of 1,4-diethylbenzene, 1,2,4-triethylbenzene, or at least one tetraethylbenzene or pentaethylbenzene as the ethylating agent, in the presence of a Lewis acid catalyst selected from the group consisting of aluminum chloride, aluminum bromide, boron trichloride, tantalum pentachloride, antimony pentafluoride, and red oil at a level of from about 0.01 to about 1 mole of the catalyst (for red oil, based on the aluminum chloride content of the red oil) per mole of the feed and at a temperature in the range of from about $-10°$ C. to about 100° C. In particular, Hagen et al., disclose that 1,2,3.4- and 1,2,3,5-tetraethylbenzenes, as well as 1,2,4.5-tetraethylbenzene (durene), are useful ethylating agents, but that hexaethylbenzene is not. Hagen et al. further disclose that 2,6-diethylnaphthalene is formed at a higher selectivity and yield when 2-ethylnaphthalene is transethylated and that pentaethylbenzene and any tetraethylbenzene are the preferred ethylating agents. However, Hagen et al. neither disclose nor suggest that the method disclosed therein would be useful for the selective ethylation to produce p-alkylethylbenzene or 4,4'-alkylethylbiphenyl.

OBJECTS OF THE INVENTION

It is therefore a general object of the present invention to provide an improved method for the highly selective production of p-alkylethylbenzene or 4,4'-alkylethylbiphenyl.

More specifically, it is an object of the present invention to provide an improved method for the highly selective production of p-ethyltoluene, p-diethylbenzene, 4,4'-diethylbiphenyl, or 4,4'-methylethylbiphenyl by ethylation under highly regiospecific conditions.

Other objects and advantages of the invention will become apparent upon reading the following detailed description and appended claims.

SUMMARY OF THE INVENTION

These objects are achieved by an improved method for producing (a) p-alkylethylbenzene, where the alkyl group is methyl or ethyl, from benzene, toluene, ethylbenzene, or a mixture of benzene and ethylbenzene as the feed or (b) a 4,4'-alkylethyldiphenyl, where the alkyl group is methyl or ethyl, from biphenyl, 4-methylbiphenyl, 4-ethylbiphenyl or a mixture of biphenyl and 4-ethylbiphenyl as the feed, comprising: reacting the feed in the liquid phase with at least one of 1,2,4-triethylbenzene, at least one tetraethylbenzene or pentaethylbenzene as the ethylating agent, at a level of from about 1 to about 10 moles of the ethylating agent per mole of the feed, in the presence of a Lewis acid or Bronsted acid alkylation catalyst or mixture thereof that is more acidic than ferric chloride and at least as acidic as ferric bromide at a level of from about 0.01 to about 1 mole of the catalyst per mole of the feed and at a temperature in the range of from about $-10°$ C. to about 100° C.

DETAILED DESCRIPTION OF THE PREFERRED EMBODIMENTS

Benzene, toluene, ethylbenzene, or a mixture of benzene and ethylbenzene is suitable for use as the feed in the method of this invention to make a p-alkylethylbenzene. Biphenyl, 4-methylbiphenyl, 4-ethylbiphenyl, or a mixture of biphenyl and 4-ethylbiphenyl is suitable for use as the feed in the method of this invention to make a 4,4'-alkylethylbiphenyl. Preferably, a feed comprising toluene or ethylbenzene is employed to make p-alkylethylbenzene or a feed comprising 4-methylbiphenyl or 4-ethylbiphenyl is employed to make 4,4'-alkylethylbiphenyl in the method of this invention. The feed must be either dissolved in a suitable solvent as described below or must be liquid at the reaction temperature employed.

As indicated in the examples hereinbelow, relative to the diethylbenzenes and 1,2,3- and 1,3,5-triethylbenzenes, polyethylated benzenes having from 3 up to 5 ethyl substituents on the benzene ring, two of which are para to one another, afford substantially improved yields of the desired p-alkylethylbenzene or 4,4'-alkylethylbiphenyl in the method of this invention. Thus, 1,2,4-triethylbenzene, any tetraethylbenzene, pentaethylbenzene, and mixtures thereof are the only suitable ethylating agents in the method of this invention. Since all tetraethylbenzenes have at least one pair of ethyl substituents that are in ring positions that are located para to each other, all tetraethylbenzenes are suitable ethylating agents in the method of this invention, and therefore, mixtures of tetraethylbenzene isomers need not be separated and can be used as the ethylating agent in the method of this invention. Hexaethylbenzene forms an irreversible addition complex with the acid catalyst, and therefore, is not an effective ethylating agent in the method of this invention. Preferably, a tetraethylbenzene, and more preferably 1,2,4,5-tetraethylbenzene, is the ethylating agent in the method of this invention.

The mole ratio of the ethylating agent-to-benzene, toluene, ethylbenzene, biphenyl, 4-methylbiphenyl or 4-ethylbiphenyl, mixture of benzene and ethylbenzene, or mixture of biphenyl and 4-ethylbiphenyl is in the range of from about 1:1, preferably from about 2:1, to about 10:1, preferable to about 5:1, in the method of this invention.

The transethylation reaction of the present invention is conducted in the liquid phase in the presence or absence of a solvent. Any liquid that is inert under the reaction conditions employed and serves as an effective solvent for the reactants and products is suitable for use in the method of this invention. Suitable solvents include halocarbons, such as methylene chloride, chlorobenzene, 1,1-dichloroethane, 1,2-dichloroethane, and chloroform, or carbon disulfide, benzene, cyclohexane, and n-octane. Solvents which are basic and bind irreversibly with the catalyst are not suitable. Such unsuitable solvents include ketones, aldehydes, ethers, esters and alcohols. Preferably, the solvent is methylene chloride. If a solvent is employed, the weight ratio of solvent-to-feed compound is in the range of from about 1:1, preferably from about 2:1, to about 15:1, preferably to about 8:1.

Lewis acids and Bronsted acids or mixtures thereof that are conventionally used as alkylation catalysts and that are more acidic than ferric chloride and at least as acidic as ferric bromide, and preferably at least as acidic as aluminum chloride, and that do not decompose under the conditions employed in the method of this invention are suitable for use as the catalyst in the method of this invention. Suitable Lewis acid catalysts include aluminum chloride, aluminum bromide, tantalum pentachloride, antimony pentafluoride, boron trichloride, ferric bromide, sulfonated zirconia, trifluoromethanesulfonic acid, and "red oil," a complex polar liquid catalyst phase which is synthesized by addition of ethyl chloride or bromide or hydrogen chloride or bromide to a slurry of aluminum chloride or some other aforesaid suitable Lewis acid in an aromatic solvent such as benzene, methylbenzene, ethylbenzene, mixed dimethylbenzenes, mixed diethylbenzenes, mixed tetramethylbenzenes or mixed tetraethylbenzenes and which forms a separate liquid phase below the phase containing the feed. Preferably, aluminum chloride or red oil containing aluminum chloride is the catalyst. Other conventional Lewis acids, such as antimony chloride, bismuth chloride, ferric chloride, tin chloride, titanium chloride, and zinc chloride, are not such effective catalysts in the method of the present invention.

The catalyst can be employed as a separate immiscible layer such as the aforementioned red oil, or it can be dissolved with the reactants and products in an organic solvent such as methylene chloride or chlorobenzene. Thus, depending upon the selection of solvent for the catalyst, the feed, ethylating agent and catalyst can be present in a single liquid phase, or the feed and catalyst can be present in separate liquid phases. In the alternative, the catalyst can be in the form of a solid, for example, aluminum chloride deposited or intercalated with graphite. The catalyst is employed in the method of this invention at a level in the range of from about 0.01, preferably from about 0.05, to about 1.0, preferably to about 0.2 mole per mole of the total content of benzene, toluene, ethylbenzene, biphenyl, 4-methylbiphenyl, 4-ethylbiphenyl, or mixture thereof.

If the reaction is performed continuously or batchwise, the residence time is from 0.1, preferably from about 1, to about 10, preferably to about 5 hours. The reaction temperature is in the range of from about $-10°$ C., preferably from about $-5°$ C., to about $100°$ C., preferably to about $20°$ C. The reaction pressure must be sufficiently high to maintain the reactants and products in the liquid phase at the particular reaction temperature employed and generally is in the range of from about 0.5, preferably from about 0.8, to about 10, preferably to about 5, atmospheres gauge.

Preferably, when a polar solvent is not used, a hydrogen halide, such as hydrogen chloride, or an alkyl, alkylene or alkylidene halide is employed as a promoter in the method of the present invention. Typically, such alkyl, alkylene, or alkylidene halides include a methyl halide, such as methyl chloride, or a methylene, ethylene, or ethylidene halide. The promoter is employed at a level of from about 0.1, preferably from about 0.5, up to about 100, preferably up to at least about 2 moles per mole of catalyst (for red oil, based on the aluminum chloride content of the red oil). When the solvent is an alkyl or alkylene halide, it also serves as a promoter in the method of the invention.

The present invention will be more clearly understood from the following specific examples:

EXAMPLES 1-47

Except as indicated hereinbelow, each of Examples 1-47 was performed using 250 milliliter, 3-neck, round-bottom flask equipped with a magnetic stirrer, purged with nitrogen and cooled in an ice bath. The components of the reaction mixture that are identified in Table 1 were introduced in the amounts and under the reaction conditions specified in Table 1. In each case, the catalyst was introduced last, at which point the transethylation reaction commenced immediately. Twenty-four hours after the catalyst was introduced, methanol, in a volume that was approximately twice the volume of the reaction medium, was introduced to quench the reaction. The product mixture was then analyzed to determine the weight percent of biphenyl, 4-methylbiphenyl or 4-ethylbiphenyl (identified as BP, 4-MBP or 4-EBP, respectively, in Table 4) that is converted, ("Conversion"), the "Yield" or mole percent of BP, 4-MBP or 4-EBP that is converted selectively to 4,4'-diethylbiphenyl or 4,4'-methylethylbiphenyl (identified as 4,4'-DEBP and 4,4'-MEBP, respectively), and the "Selectivity" or relative mole percent of 4,4'-DEBP or 4,4'-MEBP in the combined amounts of products produced in each example. The Yield is also the quotient obtained by dividing 100 into the product of the Conversion multiplied by the Selectivity. In Tables 1 and 3, TeEB means a mixture of tetraethylbenzenes.

Comparison of Examples 1-3 illustrates that high yields of the desired product are achieved even at relatively low reaction temperatures at which the reaction proceeds relatively slower, provided that the reaction is allowed to proceed long enough. Comparison of the results of Examples 6-8, 18 and 22 illustrates that the highest yields of the desired product are attained at reaction temperatures of $25°$-$30°$ C.

Comparison of the results of Examples 13 and 18 illustrates that relatively higher yields and selectivities are attained at relatively higher catalyst concentrations than at lower catalyst concentrations. The results of Examples 41-44 illustrate that strong solid acids such as sulfonated zirconia are effective catalysts in the method of this invention.

Comparison of the results of Examples 11-13 and 33-35 illustrates that the yield and selectivity for producing the desired product increase as the number of ethyl groups on the ethylating agent increases from 2 to 4 and as the ring positions of such groups with respect to one another changes from meta to ortho and then to para. Comparison of the results of Examples 13 and 15-17 illustrate that the maximum yield and selectivity for producing the desired product occur when the mole ratio of ethylating agent to feed compound is about 2:1.

Comparison of the results of Examples 2, 3, 21 and 28-31 illustrates that, when a halocarbon solvent is not employed, relatively little conversion occurs unless a promoter is employed.

TABLE 1

| Example No. | Feed | Ethylating Agent | | Catalyst | |
|---|---|---|---|---|---|
| | | Compound | Amount[1] | Compound | Amount[1] |
| 1 | BP | TeEB | 2.0 | AlCl$_3$[5] | 0.4 |
| 2 | BP | TeEB | 2.0 | AlCl$_3$[5] | 0.4 |
| 3 | BP | TeEB | 2.0 | AlCl$_3$[5] | 0.4 |
| 4 | 4-MBP | TeEB | 2.0 | AlCl$_3$[5] | 0.4 |
| 5 | 4-MBP | TeEB | 2.0 | AlCl$_3$[5] | 0.4 |
| 6 | BP | TeEB | 3.0 | AlCl$_3$[5] | 0.4 |
| 7 | BP | TeEB | 3.0 | AlCl$_3$[5] | 0.4 |
| 8 | BP | TeEB | 3.0 | AlCl$_3$[5] | 0.4 |

TABLE 1-continued

| | | | | | |
|---|---|---|---|---|---|
| 9 | 4-EBP | TeEB | 1.5 | AlCl$_3$[5] | 0.4 |
| 10 | BP | TeEB | 3.0 | AlCl$_3$[5] | 0.4 |
| 11 | 4-EBP | P-DEB | 2.0 | AlCl$_3$ | 1.0 |
| 12 | 4-EBP | 1,2,4-TEB | 2.0 | AlCl$_3$ | 1.0 |
| 13 | 4-EBP | 1,2,4,5-TeEB | 2.0 | AlCl$_3$ | 1.0 |
| 14 | BP | TeEB | 4.0 | AlCl$_3$ | 1.0 |
| 15 | 4-EBP | TeEB | 1.0 | AlCl$_3$ | 1.0 |
| 16 | 4-EBP | TeEB | 3.0 | AlCl$_3$ | 1.0 |

Footnotes
[1] moles per mole of feed
[2] dissolves reactants, product and catalyst
[3] dissolves reactants and product, but not catalyst
[4] milliliters of solvent per the actual number of moles of feed used
[5] red oil catalyst, with a separate liquid phase formed of AlCl$_3$, formed when HCl or EtBr (ethylene bromide) is passed through the C$_6$H$_{12}$ phase

| Example No. | Reaction Temp. (°) | Solvent Compound | Amount[4] | Promoter Compound | Amount |
|---|---|---|---|---|---|
| 1 | 0-20 | C$_6$H$_{12}$[3] | 80/.2 | EtBr | .4[1] |
| 2 | 20 | C$_6$H$_{12}$[3] | 80/.2 | EtBr | .4[1] |
| 3 | 30 | None | 0/.18 | HCl | Sat'd |
| 4 | 20 | C$_6$H$_{12}$[3] | 25/.01 | HCl | Sat'd |
| 5 | 20 | C$_6$H$_{12}$[3] | 25/.01 | HCl | Sat'd |
| 6 | 20 | C$_6$H$_{12}$[3] | 55/.13 | EtBr | .4[1] |
| 7 | 25-30 | C$_6$H$_{12}$[3] | 55/.13 | HCl | Sat'd |
| 8 | 40 | C$_6$H$_{12}$[3] | 50/.12 | HCl | Sat'd |
| 9 | 20 | C$_6$H$_{12}$[3] | 110/.27 | HCl | Sat'd |
| 10 | 15 | C$_6$H$_{12}$[3] | 80/.13 | HCl | Sat'd |
| 11 | 0 | CH$_2$Cl$_2$[2] | 20/.0025 | solvent | 20/.0025[4] |
| 12 | 0 | CH$_2$Cl$_2$[2] | 25/.0025 | solvent | 25/.0025[4] |
| 13 | 0 | CH$_2$Cl$_2$[2] | 30/.0025 | solvent | 30/.0025[4] |
| 14 | 0 | CH$_2$Cl$_2$[2] | 30/.0025 | solvent | 30/.0025[4] |
| 15 | 0 | CH$_2$Cl$_2$[2] | 30/.0025 | solvent | 30/.0025[4] |
| 16 | 0 | CH$_2$Cl$_2$[2] | 25/.0025 | solvent | 25/.0025[4] |

Footnotes
[1] moles per mole of feed
[2] dissolves reactants, product and catalyst
[3] dissolves reactants and product, but not catalyst
[4] milliliters of solvent per the actual number of moles of feed used
[5] red oil catalyst, with a separate liquid phase formed of AlCl$_3$ when EtBr (ethylene bromide) or HCl (hydrogen chloride) is passed through the C$_6$H$_{12}$ phase
[6] milliliters per milliliter per hour, liquid hourly space velocity.
[7] milligrams per millimole of feed

| Example No. | Feed | Ethylating Agent Compound | Amount | Catalyst Compound | Amount |
|---|---|---|---|---|---|
| 17 | 4-EBP | TeEB | 4 | AlCl$_3$ | 1.0 |
| 18 | 4-EBP | TeEB | 2 | AlCl$_3$ | 0.2 |
| 19 | 4-EBP | TeEB | 2 | AlCl$_3$ | 0.2 |
| 20 | 4-EBP | TeEB | 1 | AlCl$_3$ | 0.5 |
| 21 | 4-EBP | TeEB | 1 | AlCl$_3$ | 0.33 |
| 22 | 4-EBP | TeEB | 2 | AlCl$_3$ | 0.2 |
| 23 | 4-EBP | TeEB | 2 | AlCl$_3$ | 0.2 |
| 24 | 4-EBP | TeEB | 2 | AlCl$_3$ | 0.2 |
| 25 | 4-EBP | TeEB | 3 | AlCl$_3$ | 0.2 |
| 26 | BP | TeEB | 4 | AlCl$_3$ | 0.1 |
| 27 | 4-EBP | TeEB | 2 | AlCl$_3$ | 0.2 |
| 28 | 4-EBP | TeEB | 2 | AlCl$_3$ | 0.1 |
| 29 | BP | TeEB | 4 | AlCl$_3$ | 0.1 |
| 30 | 4-EBP | TeEB | 2 | AlCl$_3$ | 0.2 |
| 31 | BP | TeEB | 4 | AlCl$_3$ | 0.2 |
| 32 | 4-EBP | TeEB | 2 | AlCl$_3$ | 0.2 |
| 33 | BP | o-DEB | 2 | AlCl$_3$ | 0.2 |
| 34 | BP | m-DEB | 2 | AlCl$_3$ | 0.2 |

| Example No. | Reaction Temp. (°C.) | Solvent Compound | Amount[4] | Promoter Compound | Amount |
|---|---|---|---|---|---|
| 17 | 0 | CH$_2$Cl$_2$[2] | 25/.0025 | solvent | 25/.0025[4] |
| 18 | 0 | CH$_2$Cl$_2$[2] | 30/.0025 | solvent | 30/.0025[4] |
| 19 | 20 | CH$_2$Cl$_2$[2] | 30/.0025 | solvent | 30/.0025[4] |
| 20 | 0 | CH$_2$Cl$_2$[2] | 30/.005 | solvent | 30/.005[4] |
| 21 | 0 | CH$_2$Cl$_2$[2] | 30/.0075 | solvent | 30/.0075[4] |
| 22 | 20 | CH$_2$Cl$_2$[2] | 30/.0025 | solvent | 30/.0025[4] |
| 23 | reflux | CH$_2$Cl$_2$[2] | 30/.0025 | solvent | 30/.0025[4] |
| 24 | 20 | CH$_2$Cl$_2$[2] | 30/.0025 | EtBr | 1.0[1] |
| 25 | 20 | CH$_2$Cl$_2$[2] | 30/.0025 | solvent | 30/.0025[4] |
| 26 | 20 | None | 0/.005 | None | 0 |
| 27 | 20 | CH$_2$Cl$_2$[2] | 30/.0025 | solvent | 30/.0025[4] |
| 28 | 20 | None | 0/.005 | None | 0 |
| 29 | 20 | None | 0/.005 | None | 0 |
| 30 | 20 | None | 0/.005 | EtBr | 1.0[1] |
| 31 | 20 | None | 0/.005 | EtBr | 1.0[1] |
| 32 | 20 | CH$_2$Cl$_2$[2] | 1/.005 | solvent | 1/.005[4] |

TABLE 1-continued

| | | | | | | |
|---|---|---|---|---|---|---|
| 33 | 20 | $CH_2Cl_2$[2] | 30/.0025 | solvent | 30/.0025[4] | |
| 34 | 20 | $CH_2Cl_2$[2] | 30/.0025 | solvent | 30/.0025[4] | |

| Example No. | Feed | Ethylating Agent Compound | Amount[1] | Catalyst Compound | Amount[1] |
|---|---|---|---|---|---|
| 35 | BP | p-DEB | 2.0 | $AlCl_3$ | 0.2 |
| 36 | 4-EBP | TeEB | 2.0 | $AlCl_3$ | 0.1 |
| 37 | BP | TeEB | 4.0 | $AlCl_3$ | 0.1 |
| 38 | 4-EBP | TeEB | 2.0 | $AlCl_3$ | 0.2 |
| 39 | BP | TeEB | 4.0 | $AlCl_3$ | 0.2 |
| 40 | BP + 4-EBP | TeEB | 3.3 | $AlCl_3$ | 0.17 |
| 41 | 4-EBP | TeEB | 2.0 | $ZrO_2/SO_4^{-2}$ | 1.25[6] |
| 42 | 4-EBP | TeEB | 2.0 | $ZrO_2/SO_4^{-2}$ | 0.625[6] |
| 43 | 4-EBP | TeEB | 2.0 | $ZrO_2/SO_4^{-2}$ | 1.25[6] |
| 44 | BP | TeEB | 4.0 | $ZrO_2/SO_4^{-2}$ | 0.938[6] |
| 45 | BP | TeEB | 4.0 | $ZrO_2/SO_4^{-2}$ | 0.938[6] |
| 46 | 4-EBP | TeEB | 2.0 | $ZrO_2/SO_4^{-2}$ | 40[7] |
| 47 | BP + 4-EBP | TeEB | 3.3 | $ZrO_2/SO_4^{-2}$ | 33.3[7] |

| Example No. | Reaction Temp. °C. | Solvent Compound | Amount[4] | Promoter Compound | Amount |
|---|---|---|---|---|---|
| 35 | 20 | $CH_2Cl_2$[2] | 30/.0025 | None | 0 |
| 36 | 20 | None | 0/.005 | EtBr | .1[1] |
| 37 | 20 | None | 0/.005 | EtBr | .1[1] |
| 38 | 20 | $CH_2Cl_2$[2] | 30/.0025 | EtBr | .2[1] |
| 39 | 20 | $CH_2Cl_2$[2] | 30/.0025 | solvent | 30/.0025[4] |
| 40 | 20 | $CH_2Cl_2$[2] | 30/.0025 + .0005 | solvent | 30/.0025 + .0005[4] |
| 41 | 20 | $CH_2Cl_2$[2] | 24/.0025 | solvent | 24/.0025[4] |
| 42 | 20 | $CH_2Cl_2$[2] | 24/.0025 | solvent | 24/.0025[4] |
| 43 | 20 | $CH_2Cl_2$[2] | 24/.0025 | solvent | 24/.0025[4] |
| 44 | 20 | $CH_2Cl_2$[2] | 12/.0025 | solvent | 12/.0025[4] |
| 45 | 20 | None | 0/.010 | none | 0 |
| 46 | 20 | $CH_2Cl_2$[2] | 30/.0025 | solvent | 30/.0025[4] |
| 47 | 20 | $CH_2Cl_2$[2] | 30/.0025 + .0005 | solvent | 30/.0025[4] + .0005 |

TABLE 2

| Example No. | Reaction Time (min) | Conversion | Desired Product Compound | Yield | Selectivity |
|---|---|---|---|---|---|
| 1 | 420 | 4.56 | 4,4'-DEBP | 4.56 | 100 |
| | 660 | 16.90 | | 16.25 | 96.1 |
| | 960 | 32.71 | | 30.66 | 93.8 |
| | 1500 | 57.17 | | 51.52 | 98.11 |
| | 3240 | 72.70 | | 63.08 | 86.76 |
| 2 | 90 | 7.68 | 4,4'-DEBP | 7.54 | 98.13 |
| | 180 | 26.91 | | 25.39 | 94.32 |
| | 300 | 44.41 | | 40.73 | 91.71 |
| | 540 | 51.49 | | 46.92 | 91.13 |
| | 2070 | 67.53 | | 59.35 | 87.89 |
| 3 | 120 | 13.89 | 4,4'-DEBP | 13.36 | 96.23 |
| | 240 | 33.65 | | 31.33 | 93.09 |
| | 540 | 57.84 | | 51.63 | 89.25 |
| | 960 | 68.50 | | 59.76 | 87.25 |
| | 1530 | 78.88 | | 66.13 | 83.84 |
| 4 | 30 | 10.59 | 4,4'-MEBP | 10.42 | 98.36 |
| | 60 | 20.32 | | 19.93 | 98.06 |
| | 180 | 51.08 | | 47.32 | 92.65 |
| | 870 | 84.68 | | 65.82 | 77.73 |
| 5 | 60 | 10.14 | 4,4'-MEBP | 10.14 | 100.00 |
| | 120 | 21.31 | | 21.08 | 98.91 |
| | 180 | 33.19 | | 32.18 | 96.96 |
| | 360 | 44.08 | | 42.16 | 95.64 |
| | 720 | 61.70 | | 57.09 | 92.53 |
| | 1320 | 81.69 | | 70.92 | 86.81 |
| 6 | 90 | 13.62 | 4,4'-DEBP | 13.22 | 97.02 |
| | 150 | 33.40 | | 31.51 | 94.33 |
| | 330 | 60.70 | | 55.29 | 91.10 |
| | 630 | 66.69 | | 60.04 | 90.03 |
| | 690 | 93.50 | | 60.68 | 64.90 |
| 7 | 30 | 25.14 | 4,4'-DEBP | 23.48 | 93.40 |
| | 60 | 45.59 | | 41.80 | 91.67 |
| | 120 | 60.99 | | 54.32 | 89.06 |
| | 210 | 72.83 | | 63.11 | 86.66 |
| | 870 | 89.70 | | 72.78 | 81.14 |
| | 1260 | 94.65 | | 69.28 | 73.20 |
| 8 | 30 | 10.27 | 4,4'-DEBP | 9.83 | 95.70 |
| | 60 | 21.06 | | 19.66 | 93.39 |
| | 120 | 29.48 | | 26.93 | 91.33 |
| | 300 | 40.73 | | 35.40 | 86.93 |
| | 600 | 64.89 | | 50.68 | 78.10 |
| | 1120 | 80.80 | | 60.68 | 75.10 |
| 9 | 45 | 6.03 | 4,4'-DEBP | 6.03 | 100.00 |
| | 90 | 16.21 | | 15.84 | 97.74 |
| | 510 | 62.89 | | 58.22 | 92.57 |
| | 1050 | 75.42 | | 67.86 | 89.97 |
| 10 | 120 | 3.88 | 4,4'-DEBP | 3.88 | 100.00 |
| | 180 | 9.88 | | 9.70 | 98.19 |
| | 300 | 23.33 | | 22.07 | 94.62 |
| | 480 | 39.90 | | 36.36 | 93.45 |
| | 960 | 53.60 | | 49.42 | 92.19 |
| | 1495 | 67.03 | | 60.41 | 90.11 |
| 11 | 30 | 56.3 | 4,4'-DEBP | 39.9 | 70.9 |
| | 60 | 49.2 | | 40.8 | 83.0 |
| | 90 | 58.2 | | 34.2 | 58.8 |
| | 210 | 60.4 | | 30.5 | 50.4 |
| | 1200 | 76.6 | | 39.3 | 51.4 |
| 12 | 30 | 48.9 | 4,4'-DEBP | 45.7 | 93.5 |
| | 60 | 63.3 | | 57.5 | 90.9 |
| | 120 | 70.9 | | 64.4 | 90.8 |
| | 240 | 75.7 | | 65.7 | 86.8 |
| 13 | 30 | 30.1 | 4,4'-DEBP | 27.2 | 90.8 |
| | 60 | 61.7 | | 55.1 | 89.3 |
| | 120 | 77.7 | | 71.2 | 91.6 |
| | 210 | 90.2 | | 86.9 | 96.4 |
| | 240 | 89.4 | | 86.1 | 96.3 |
| 14 | 30 | 13.76 | 4,4'-DEBP | 4.75 | 34.52 |
| | 90 | 44.25 | | 30.3 | 68.60 |
| | 150 | 55.96 | | 40.69 | 72.71 |
| | 210 | 74.21 | | 58.50 | 78.83 |
| | 420 | 94.52 | | 70.32 | 74.40 |
| 15 | 30 | 18.1 | 4,4'-DEBP | 15.8 | 87.2 |
| | 60 | 40.9 | | 33.7 | 82.3 |
| | 90 | 56.6 | | 47.4 | 83.7 |
| | 120 | 65.7 | | 54.9 | 83.6 |
| | 420 | 88.7 | | 70.7 | 79.7 |

TABLE 2-continued

| Example No. | Reaction Time (min) | Conversion | Desired Product Compound | Yield | Selectivity |
|---|---|---|---|---|---|
| 16 | 30 | 31.4 | 4,4'-DEBP | 22.8 | 72.8 |
|  | 60 | 54.3 |  | 42.7 | 78.7 |
|  | 120 | 73.3 |  | 60.3 | 82.3 |
|  | 180 | 84.8 |  | 72.1 | 85.1 |
|  | 420 | 97.4 |  | 75.8 | 77.9 |
| 17 | 30 | 30.3 | 4,4'-DEBP | 22.8 | 75.3 |
|  | 60 | 49.9 |  | 39.8 | 79.8 |
|  | 90 | 63.3 |  | 50.8 | 80.2 |
|  | 180 | 84.6 |  | 62.3 | 73.6 |
|  | 420 | 98.2 |  | 51.2 | 52.2 |
| 18 | 30 | 6.7 | 4,4'-DEBP | 2.2 | 32.8 |
|  | 60 | 12.2 |  | 7.1 | 58.2 |
|  | 90 | 23.1 |  | 17.2 | 74.5 |
|  | 180 | 35.1 |  | 29.2 | 83.1 |
|  | 240 | 42.1 |  | 36.3 | 86.3 |
|  | 420 | 54.0 |  | 49.0 | 90.7 |
|  | 1200 | 63.1 |  | 50.8 | 80.5 |
| 19 | 30 | 34.8 | 4,4'-DEBP | 27.6 | 79.4 |
|  | 60 | 49.7 |  | 42.4 | 85.4 |
|  | 90 | 57.1 |  | 51.5 | 90.2 |
|  | 240 | 69.4 |  | 65.4 | 94.3 |
|  | 1200 | 80.3 |  | 63.2 | 78.8 |
| 20 | 30 | 6.4 | 4,4'-DEBP | 2.8 | 43.1 |
|  | 90 | 26.3 |  | 20.1 | 76.3 |
|  | 180 | 49.7 |  | 39.0 | 78.5 |
|  | 240 | 60.1 |  | 46.9 | 78.0 |
|  | 420 | 86.7 |  | 60.0 | 69.2 |
| 21 | 30 | 11.0 | 4,4'-DEBP | 6.9 | 62.6 |
|  | 90 | 33.4 |  | 25.9 | 77.4 |
|  | 180 | 54.1 |  | 43.8 | 80.9 |
|  | 240 | 62.0 |  | 50.2 | 80.9 |
|  | 420 | 85.0 |  | 63.4 | 74.6 |
| 22 | 24 | 76.3 | 4,4'-DEBP | 60.4 | 79.2 |
|  | 42 | 77.2 |  | 61.0 | 79.1 |
| 23 | 30 | 9.2 | 4,4'-DEBP | 3.3 | 36.4 |
|  | 60 | 16.0 |  | 9.7 | 60.8 |
|  | 90 | 15.5 |  | 9.6 | 62.1 |
|  | 120 | 16.0 |  | 10.3 | 64.5 |
| 24 | 30 | 5.4 | 4,4'-DEBP | 0.8 | 14.1 |
|  | 90 | 18.5 |  | 11.4 | 61.6 |
|  | 180 | 59.6 |  | 47.9 | 80.4 |
|  | 420 | 77.3 |  | 61.1 | 79.1 |
|  | 1200 | 80.3 |  | 66.3 | 82.6 |
| 25 | No Reaction | 0 | 4,4'-DEBP | 0 | 0 |
| 26 | No Reaction | 0 | 4,4'-DEBP | 0 | 0 |
| 27 | 90 | 77.3 | 4,4'-DEBP | 60.9 | 78.9 |
| 28 | No Reaction | 0 | 4,4'-DEBP | 0 | 0 |
| 29 | No Reaction | 0 | 4,4'-DEBP | 0 | 0 |
| 30 | No Reaction | 0 | 4,4'-DEBP | 0 | 0 |
| 31 | No Reaction | 0 | 4,4'-DEBP | 0 | 0 |
| 32 | No Reaction | 0 | 4,4'-DEBP | 0 | 0 |
| 33 | 30 | 11.8 | 4,4'-DEBP | 5.2 | 43.8 |
|  | 90 | 21.1 |  | 10.2 | 48.1 |
|  | 180 | 30.8 |  | 15.6 | 50.7 |
|  | 360 | 36.9 |  | 18.1 | 49.0 |
| 34 | 30 | 5.3 | 4,4'-DEBP | 0.7 | 4.4 |
|  | 60 | 10.1 |  | 3.0 | 29.4 |
|  | 90 | 15.9 |  | 5.6 | 35.5 |
|  | 120 | 24.0 |  | 8.9 | 37.2 |
|  | 180 | 31.7 |  | 12.4 | 39.2 |
|  | 360 | 43.8 |  | 18.4 | 42.0 |
| 35 | 30 | 32.6 | 4,4'-DEBP | 20.8 | 63.9 |
|  | 60 | 47.7 |  | 30.0 | 62.9 |
|  | 120 | 58.9 |  | 34.2 | 58.1 |
|  | 240 | 63.6 |  | 35.2 | 55.4 |
|  | 360 | 66.3 |  | 21.9 | 33.1 |
| 36 | No Reaction | 0 | 4,4'-DEBP | 0 | 0 |
| 37 | No Reaction | 0 | 4,4'-DEBP | 0 | 0 |
| 38 | No Reaction | 0 | 4,4'-DEBP | 0 | 0 |
| 39 | 30 | 25.1 | 4,4'-DEBP | 7.0 | 27.8 |
|  | 60 | 34.4 |  | 13.9 | 40.5 |
|  | 120 | 40.8 |  | 21.5 | 52.8 |
|  | 240 | 51.1 |  | 29.5 | 57.8 |
|  | 1440 | 59.0 |  | 35.5 | 60.1 |
| 40 | 30 | 33.7 | 4,4'-DEBP | 17.5 | 52.0 |
|  | 60 | 45.5 |  | 27.9 | 61.3 |
|  | 120 | 59.2 |  | 38.6 | 65.2 |
|  | 240 | 70.7 |  | 47.8 | 67.6 |
|  | 1440 | 80.2 |  | 53.1 | 66.2 |
| 41 | 60 | 34.3 | 4,4'-DEBP | 29.5 | 85.9 |
|  | 120 | 17.7 |  | 14.6 | 82.3 |
|  | 180 | 10.9 |  | 8.2 | 74.9 |
|  | 240 | 10.1 |  | 8.1 | 90.2 |
| 42 | 15 | 79.3 | 4,4'-DEBP | 63.3 | 79.8 |
|  | 75 | 74.4 |  | 61.7 | 82.9 |
|  | 135 | 35.2 |  | 29.4 | 83.6 |
|  | 195 | 18.9 |  | 15.3 | 80.8 |
|  | 255 | 13.1 |  | 10.8 | 82.4 |
| 43 | 15 | 60.2 | 4,4'-DEBP | 51.6 | 85.7 |
|  | 135 | 36.7 |  | 31.9 | 86.8 |
|  | 195 | 22.8 |  | 19.3 | 84.5 |
|  | 255 | 18.9 |  | 15.4 | 81.2 |
| 44 | 15 | 6.6 | 4,4'-DEBP | 1.9 | 28.9 |
| 45 | No Reaction | 0 | 4,4'-DEPP | 0 | 0 |
| 46 | No Reaction | 0 | 4,4'-DEBP | 0 | 0 |
| 47 | No Reaction | 0 | 4,4'-DEBP | 0 | 0 |

EXAMPLES 48–65

Except as indicated hereinbelow, each of Examples 48–65 was performed using 250 milliliter, 3-neck, round-bottom flask equipped with a magnetic stirrer, purged with nitrogen and cooled in an ice bath. The components of the reaction mixture that are identified in Table 3 were introduced in the amounts and under the reaction conditions specified in Table 3. In each case, the catalyst was introduced last, at which point the transethylation reaction commenced immediately. Twenty-four hours after the catalyst was introduced, methanol, in a volume that was approximately twice the volume of the reaction medium, was introduced to quench the reaction. The product mixture was then analyzed to determine the weight percent of toluene or ethylbenzene (identified as TOL and EB, respectively, in Table 3) that is converted ("Conversion"), the "Yield" or mole percent of TOL or EB that is converted selectively to p-methylethylbenzene or p-diethylbenzene (identified as p-MEB or p-DEB, respectively), and the "Selectivity" or relative mole percent of p-MEB or p-DEB in the combined amounts of products produced in each example. The Yield is also the quotient obtained by dividing 100 into the product of the Conversion multiplied by the Selectivity.

When ethylbenzene is the feed, comparison of the results of Examples 48–50 illustrates that the use of reactants at a mole ratio of 1.5:1 of ethylating agent-to-feed compound affords the highest yield and selectivity of the desired product, and comparison of the results of Examples 54–56 illustrates that the use of a higher catalyst concentration affords a higher yield and selectivity for the desired product. By contrast, when methylbenzene is the feed, comparison of the results of Examples 57–59 illustrates that comparable yields and selectivities of the desired product are obtained even when the mole ratio of ethylating agent-to-feed compound was varied from 1:1 to 2:1, and comparison of the results of Examples 63–65 illustrates that similar yield and selectivities of the desired product are obtained even when the concentration of the catalyst was varied from a high level to a low level.

Comparison of the results of Examples 49, 52, 58 and 60 illustrates that the use of tetraethylbenzene instead of triethylbenzene as the ethylating agent affords greater yields and selectivities of the desired product regardless of whether ethylbenzene or methylbenzene is the feed compound. Comparison of the results of Examples 57, 58, 61, and 62 illustrates that, even though the reaction rate is higher at higher reaction temperatures, the yields and selectivities for the desired product obtained at lower reaction temperatures are comparable to those obtained at higher reaction temperatures if the reaction is allowed to proceed for a long enough period.

Comparison of the results of Examples 50 and 57 illustrates that comparable yields and selectivities of the desired product are obtained when the reaction system involves a single liquid phase in a methylene chloride solvent or two liquid phases with no solvent.

TABLE 3

| Example No. | Feed | Ethylating Agent Compound | Amount[1] | Catalyst Compound | Amount[1] |
|---|---|---|---|---|---|
| 48 | EB | TeEB | 2.0 | $AlCl_3$[5] | 0.4 |
| 49 | EB | TeEB | 1.0 | $AlCl_3$[5] | 0.4 |
| 50 | EB | TeEB | 1.5 | $AlCl_3$[5] | 0.4 |
| 51 | EB | TeEB | 2.0 | $AlCl_3$[5] | 0.4 |
| 52 | EB | 1,2,4-TEB | 1.0 | $AlCl_3$[5] | 0.4 |
| 53 | EB | TeEB | 2.0 | $AlCl_3$[5] | 0.4 |
| 54 | EB | TeEB | 2.0 | $AlCl_3$ | 1.0 |
| 55 | EB | TeEB | 2.0 | $AlCl_3$ | 0.2 |
| 56 | EB | TeEB | 1.5 | $AlCl_3$ | 0.5 |
| 57 | TOL | TeEB | 2.0 | $AlCl_3$[5] | 0.4 |
| 58 | TOL | TeEB | 1.0 | $AlCl_3$[5] | 0.4 |
| 59 | TOL | TeEB | 1.5 | $AlCl_3$[5] | 0.4 |
| 60 | TOL | 1,2,4-TEB | 1.0 | $AlCl_3$[5] | 0.4 |
| 61 | TOL | TeEB | 1.0 | $AlCl_3$[5] | 0.4 |
| 62 | TOL | TeEB | 2.0 | $AlCl_3$[5] | 0.4 |
| 63 | TOL | TeEB | 2.0 | $AlCl_3$[5] | 0.2 |
| 64 | TOL | TeEB | 2.0 | $AlCl_3$ | 1.0 |
| 65 | TOL | TeEB | 2.0 | $AlCl_3$ | 1.0 |

Footnotes
[1] moles per mole of feed
[2] dissolves reactants, product and catalyst
[3] dissolves reactants and product, but not catalyst
[4] milliliters of solvent per mole of feed
[5] red oil catalyst, with a separate liquid phase formed of $AlCl_3$ when HCl is passed through the $C_6H_{12}$ phase

| Example No. | Reaction Temp. (°C.) | Solvent Compound | Amount[4] | Promoter Compound | Amount |
|---|---|---|---|---|---|
| 48 | 20 | $C_6H_{12}$[3] | 20/.047 | HCl | sat'd |
| 49 | 20 | $C_6H_{12}$[3] | 20/.141 | HCl | sat'd |
| 50 | 20 | None | 0/.267 | EtBr | 0.4[1] |
| 51 | 0 | None | 0/.196 | EtBr | 0.4[1] |
| 52 | 20 | $C_6H_{12}$[3] | 20/.062 | HCl | sat'd |
| 53 | 0 | None | 0/.134 | EtBr | 0.4[1] |
| 54 | 0 | $CH_2Cl_2$[2] | 30/.0025 | solvent | 30/.0025[4] |
| 55 | 20 | $CH_2Cl_2$[2] | 30/.0025 | solvent | 30/.0025[4] |
| 56 | 20 | $CH_2Cl_2$[2] | 30/.0025 | solvent | 30/.0025[4] |
| 57 | 20 | None | 0/.892 | HCl | sat'd |
| 58 | 20 | None | 0/.892 | HCl | sat'd |
| 59 | 20 | None | 0/.089 | HCl | sat'd |
| 60 | 20 | $C_6H_{12}$ | 20/.062 | HCl | sat'd |
| 61 | 0-15 | None | 0/.268 | EtBr | 0.4[1] |
| 62 | 0 | None | 0/.196 | EtBr | 0.4[1] |
| 63 | 20 | $CH_2Cl_2$[2] | 30/.0025 | solvent | 30/.0025[4] |
| 64 | 0 | $CH_2Cl_2$[2] | 30/.0025 | solvent | 30/.0025[4] |
| 65 | 0 | $CH_2Cl_2$[2] | 30/.0025 | solvent | 30/.0025[4] |

Footnotes
[1] moles per mole of feed
[2] dissolves reactants, product and catalyst
[3] dissolves reactants and product, but not catalyst
[4] milliliters of solvent per the actual number of moles of feed used
[5] red oil catalyst, with a separate liquid phase formed of $AlCl_3$ when HCl or EtBr is passed through the $C_6H_{12}$ phase

TABLE 4

| Example No. | Reaction Time (min) | Conversion | Desired Product Compound | Yield | Selectivity |
|---|---|---|---|---|---|
| 48 | 30 | 17.00 | p-DEB | 14.39 | 84.65 |
|  | 60 | 37.68 |  | 31.57 | 37.68 |
|  | 90 | 57.78 |  | 47.88 | 82.87 |
|  | 130 | 76.26 |  | 61.27 | 81.52 |
|  | 225 | 94.66 |  | 71.28 | 75.30 |
| 49 | 30 | 67.75 | p-DEB | 38.19 | 56.38 |
|  | 60 | 72.95 |  | 37.25 | 51.06 |
|  | 90 | 75.05 |  | 35.36 | 47.12 |
|  | 360 | 80.06 |  | 26.21 | 32.74 |
| 50 | 30 | 44.09 | p-DEB | 36.07 | 81.80 |
|  | 60 | 79.81 |  | 63.15 | 79.13 |
|  | 90 | 91.87 |  | 68.83 | 74.92 |
|  | 240 | 96.34 |  | 55.41 | 57.52 |
| 51 | 30 | 9.91 | p-DEB | 7.68 | 77.56 |
|  | 60 | 16.96 |  | 13.87 | 81.76 |
|  | 90 | 23.45 |  | 19.57 | 83.47 |
|  | 135 | 33.98 |  | 28.88 | 84.99 |
|  | 225 | 59.98 |  | 49.83 | 83.08 |
|  | 480 | 95.37 |  | 70.10 | 73.51 |
| 52 | 30 | 67.77 | p-DEB | 26.60 | 39.25 |
|  | 60 | 68.94 |  | 24.76 | 35.92 |
|  | 90 | 69.56 |  | 23.43 | 33.68 |

TABLE 4-continued

| Example No. | Reaction Time (min) | Conversion | Desired Product Compound | Yield | Selectivity |
|---|---|---|---|---|---|
| | 210 | 70.50 | | 21.23 | 30.12 |
| | 405 | 71.97 | | 21.30 | 29.60 |
| 53 | 30 | 0 | p-DEB | 0 | 0 |
| | 60 | 0 | | 0 | 0 |
| | 90 | 0 | | 0 | 0 |
| 54 | 30 | 0.8 | p-DEB | 0.6 | 74.2 |
| | 60 | 11.7 | | 9.8 | 83.7 |
| | 120 | 87.0 | | 67.8 | 78.0 |
| | 180 | 92.7 | | 67.5 | 72.8 |
| | 240 | 97.5 | | 43.5 | 44.6 |
| 55 | 30 | 0 | p-DEB | 0 | 0 |
| | 60 | 0 | | 0 | 0 |
| | 90 | 0 | | 0 | 0 |
| 56 | 30 | 26.6 | p-DEB | 20.0 | 75.3 |
| | 60 | 90.5 | | 66.7 | 73.6 |
| | 90 | 92.5 | | 61.7 | 66.7 |
| | 120 | 93.4 | | 57.3 | 61.3 |
| | 240 | 95.3 | | 47.1 | 49.5 |
| | 1440 | 96.7 | | 38.2 | 39.5 |
| 57 | 30 | 23.50 | p-MEB | 17.4 | 73.9 |
| | 60 | 68.83 | | 50.4 | 73.3 |
| | 90 | 88.51 | | 50.6 | 57.2 |
| | 165 | 98.12 | | 28.75 | 29.30 |
| 58 | 30 | 15.87 | p-MEB | 14.0 | 88.4 |
| | 60 | 44.25 | | 38.6 | 87.2 |
| | 90 | 71.01 | | 56.5 | 79.6 |
| | 210 | 94.18 | | 26.18 | 27.80 |
| 59 | 30 | 8.81 | | 6.48 | 73.5 |
| | 60 | 24.56 | p-MEB | 20.78 | 84.6 |
| | 90 | 52.29 | | 43.36 | 82.9 |
| | 120 | 77.92 | | 56.93 | 73.07 |
| | 180 | 96.28 | | 41.45 | 43.05 |
| 60 | 30 | 72.70 | p-MEB | 31.1 | 42.8 |
| | 60 | 76.28 | | 27.1 | 35.6 |
| | 90 | 78.54 | | 24.3 | 30.9 |
| | 210 | 82.38 | | 18.3 | 22.2 |
| | 360 | 85.25 | | 14.8 | 17.4 |
| 61 | 30 | 4.29 | p-MEB | 2.11 | 49.0 |
| | 60 | 5.03 | | 2.97 | 59.0 |
| | 120 | 7.13 | | 4.60 | 64.5 |
| | 405 | 52.98 | | 42.49 | 80.21 |
| | 535 | 63.18 | | 49.83 | 78.87 |
| | 655 | 84.82 | | 58.78 | 69.30 |
| | 775 | 92.56 | | 51.20 | 55.32 |
| 62 | 30 | 7.24 | p-MEB | 4.6 | 63.7 |
| | 60 | 11.59 | | 8.1 | 69.8 |
| | 150 | 31.49 | | 25.0 | 79.3 |
| | 240 | 43.12 | | 35.92 | 83.30 |
| | 300 | 50.98 | | 41.79 | 81.96 |
| | 360 | 58.33 | | 46.86 | 80.33 |
| | 575 | 87.48 | | 47.41 | 54.20 |
| 63 | 30 | 1.50 | p-MEB | 1.5 | 100 |
| | 90 | 22.40 | | 36.5 | 81.0 |
| | 120 | 45.10 | | 20.0 | 89.3 |
| | 180 | 72.4 | | 53.3 | 73.6 |
| | 240 | 84.0 | | 53.4 | 66.5 |
| 64 | 30 | 0 | p-MEB | 0 | 0 |
| | 90 | 3.00 | | 3.0 | 100.0 |
| | 120 | 62.1 | | 45.6 | 73.5 |
| | 180 | 80.7 | | 53.1 | 65.8 |
| | 240 | 91.9 | | 48.0 | 52.3 |
| | 360 | 98.6 | | 12.6 | 12.8 |
| 65 | 30 | 68.6 | p-MEB | 49.8 | 72.6 |

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A method for producing (a) a p-alkylethylbenzene, wherein the alkyl group is methyl or ethyl, from benzene, toluene, ethylbenzene, or a mixture of benzene and ethylbenzene as the feed or (b) a 4,4'-alkylethylbiphenyl, wherein the alkyl group is methyl or ethyl, from biphenyl, 4-methylbiphenyl, 4-ethylbiphenyl or a mixture of biphenyl and 4-ethylbiphenyl as the feed comprising: reacting the feed in the liquid phase with at least one of 1,2,4-triethylbenzene, at least one tetraethylbenzene or pentaethylbenzene as the ethylating agent, at a level of from about 1 to about 10 moles of the ethylating agent per mole of the feed, in the presence of a catalyst comprising a Lewis acid or Bronsted acid alkylation catalyst or mixture thereof that is more acidic than ferric chloride and at least as acidic as ferric bromide, at a level of from about 0.01 to about 1 mole of the catalyst per mole of the feed and at a temperature from about −10° C. to about 100° C.

2. The method of claim 1 wherein the feed comprises biphenyl, 4-methylbiphenyl, 4-ethylbiphenyl, or a mixture of biphenyl and 4-ethylbiphenyl.

3. The method of claim 1 wherein the feed comprises benzene, toluene, ethylbenzene, or a mixture of benzene and ethylbenzene.

4. The method of claim 1 wherein the ethylating agent is a tetraethylbenzene, pentaethylbenzene, or a mixture thereof.

5. The method of claim 1 wherein the ethylating agent is at a level of from about 2 to about 5 moles per mole of the feed by weight.

6. The method of claim 1 wherein the catalyst comprises aluminum chloride, aluminum bromide, boron trichloride, tantalum pentachloride, antimony pentafluoride, ferric bromide, sulfonated zirconia, trifluoromethanesulfonic acid or red oil.

7. The method of claim 1 wherein the catalyst comprises aluminum chloride or red oil.

8. The method of claim 7 wherein the catalyst is at a level of from 0.05 to about 0.2 mole per mole of the feed.

9. The method of claim 1 wherein the reaction is conducted at a temperature in the range of from about −5° C. to about 20° C.

10. The method of claim 1 wherein the reaction is conducted in the presence of a promoter comprising a hydrogen halide or an alkyl, alkylene or alkylidene halide, at a level of from about 0.1 to about 100 moles per mole of the catalyst.

11. The method of claim 10 wherein the promoter is hydrogen chloride or methylene chloride.

12. The method of claim 1 wherein the feed and ethylating agent are dissolved in a solvent.

13. The method of claim 1 wherein the catalyst is dissolved in a solvent.

14. The method of claim 1 wherein the feed, ethylating agent and catalyst are present in a single liquid phase.

15. The method of claim 1 wherein the feed and catalyst are present in separate liquid phases.

16. The method of claim 1 wherein the catalyst is in the solid phase.

* * * * *